United States Patent
Hayashi et al.

(10) Patent No.: US 6,221,544 B1
(45) Date of Patent: Apr. 24, 2001

(54) INSPECTING METHOD OF COLOR FILTER AND MANUFACTURING METHOD OF COLOR FILTER

(75) Inventors: Satoshi Hayashi, Kawasaki; Hiroshi Fujiike, Yokohama; Yoshitomo Marumoto, Kawasaki, all of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/471,081

(22) Filed: Dec. 23, 1999

(30) Foreign Application Priority Data

Dec. 28, 1998 (JP) .................................. 10-372129

(51) Int. Cl.[7] ............................ G02B 5/20; G02F 1/1335; G01M 11/00
(52) U.S. Cl. ............................ 430/7; 356/239.2; 356/433; 349/106; 347/107
(58) Field of Search ............................ 430/7; 356/239.2, 356/433, 406, 408, 425; 349/106; 347/106, 107; 427/164, 553

(56) References Cited

U.S. PATENT DOCUMENTS 5,400,135 * 3/1995 Maeda .................................. 356/237
5,773,173 * 6/1998 Nakano et al. ..................... 430/30

FOREIGN PATENT DOCUMENTS

| 9-043097 | * | 2/1997 | (JP) . |
| 10-142101 | * | 5/1998 | (JP) . |
| 10-315510 | * | 11/1998 | (JP) . |
| 11-006786 | * | 1/1999 | (JP) . |

* cited by examiner

Primary Examiner—John A. McPherson
(74) Attorney, Agent, or Firm—Fitzpatrick, Cella, Harper & Scinto

(57) ABSTRACT

In an inspecting method of a color filter, comprising irradiating light from a light source to a coloring portion, measuring a transmitting light amount transmitted through the coloring portion by a light receiving element, and calculating a coloring density of the coloring portion, the light amount of the light source is set substantially constant, the amount of incident light received by the light receiving element is adjusted by an optical element arranged within an optical path, the transmitting light amount of an uncoloring portion is measured and the coloring density of the coloring portion is inspected by comparing the transmitting light amount of the coloring portion to the transmitting light amount of the uncoloring portion.

6 Claims, 7 Drawing Sheets

INSPECTING METHOD OF COLOR FILTER AND MANUFACTURING METHOD OF COLOR FILTER

BACKGROUND OF THE INVENTION

1. Field of the Invention

The present invention relates to an inspecting method of a color filter for inspecting the coloring density of a coloring portion of the color filter at high speed with high accuracy, and a manufacturing method of the color filter utilizing this inspecting method.

2. Related Background Art

A color filter constituting a liquid crystal display unit is generally constructed by arranging coloring portions colored in red (R), green (G) and blue (B) as three primary colors of light on a transparent substrate. A dyeing method, a pigment dispersing method, an electrodepositing method, etc. are conventionally used as a manufacturing method of the color filter. However, an ink jet system simple in process and economically advantageous has recently been used.

When a coloring portion is formed by using the ink jet system, ink is individually given to predetermined areas. Therefore, unlike the other systems, a problem of uneven coloring is caused by the density distribution in the coloring portions. A defect of the uneven coloring is more than visually recognizable even when this density distribution is only several %, depending on a color of the coloring portion. Accordingly, in a manufacturing process of the color filter using the ink jet system, it is required that these color irregularities are discriminated with high accuracy and an ink amount to be given is further controlled on the basis of the results of this discrimination.

In an inspection of the color irregularities of the color filter, generally, an absolute value of the coloring density is a problem as well as the color irregularities. Therefore, a reference light amount is adjusted. In the reference light amount adjustment, a transmitting light amount is adjusted in a transparent (no light shielding layer such as a black matrix, etc. exists) uncoloring portion within a non-display area. An amount of incident light entering to a CCD camera at an adjusting time of this reference light amount reaches two to five times an amount of incident light entering to the CCD camera when the transmitting light amount of the coloring portion is measured. Therefore, when a light amount of the light source is set such that this light amount is equal to or smaller than a light amount providing a full output of the CCD camara at the time of the reference light amount adjusting, only a light amount of ⅕ to ½ times this set light amount is entered to the CCD camera at a measuring time of the coloring portion. Therefore, a reduction in S/N is caused by a dark electric current of the CCD, etc. In particular, in the inspection of the uneven coloring in the color filter, it is necessary to discriminate the amount of incident light entered from a transmitting light amount equal to or smaller than 1% in the coloring portion of the same color. Therefore, it is necessary to avoid this reduction in S/N. To avoid this reduction, it is considered that the light amount of the light source at the measurement time of the coloring portion is increased.

However, when the light amount of the light source is adjusted, the light amount is unstable for some time after the adjustment. As described above, it is necessary to discriminate the coloring density distribution at a level of several %. Accordingly, such an unstable light amount just after the adjustment of the light amount causes an error in measurement. Therefore, when the light amount is adjusted, it is necessary to take time until the light amount is stabilized, which is an obstacle in improving efficiency by shortening an inspecting time.

SUMMARY OF THE INVENTION

An object of the present invention is to provide an inspecting method capable of inspecting uneven coloring of a color filter at high speed with high accuracy, a manufacturing method of the color filter with the use of an ink jet system in which the uneven coloring are reduced by utilizing this inspecting method, and an inspecting method of the color filter in the ink jet system.

The present invention resides in an inspecting method of a color filter comprising: irradiating with light from a light source a coloring portion; measuring a transmitting light amount transmitted through the coloring portion by a light receiving element; and calculating a coloring density of the coloring portion; in which the light amount of the light source is set substantially constant, the amount of incident light received by the light receiving element is adjusted by an optical element arranged within an optical path, the transmitting light amount of an uncoloring portion is measured and the coloring density of the coloring portion is inspected by comparing the transmitting light amount of the coloring portion to the transmitting light amount of the uncoloring portion.

In the present invention, the light amount is adjusted by using the optical element, and the light amount of the light source is made constant. Therefore, an error in measurement due to an unstable light amount caused by the adjustment of the light amount of the light source is prevented. Accordingly, no time for stabilization after the adjustment of the light amount is required. In the present invention, the amount of incident light received by the light receiving element can be easily adjusted to a light amount suitable for the light reception of this light receiving element by using the optical element. Therefore, the measurement can be precisely made by the same light receiving element. Particularly, when an ink amount to be given is controlled on the basis of the results of an inspection of uneven coloring, it is necessary to correlate an absolute value in one measurement with an absolute value in another measurement. Therefore, it is necessary to adjust the light amount by measuring a reference before each measurement. Namely, it is necessary to measure the light amount value of a transparent uncoloring portion within a non-display area and adjust this light amount value to a constant value so as to remove elements except for coloring. In this case, the transmitting light amounts of the coloring and uncoloring portions are greatly different from each other. However, in the present invention, the amount of incident light or the transmitting light amount is adjusted by the optical element, so that the transmitting light amounts of the coloring and uncoloring portions can be precisely measured by the same light receiving element.

DETAILED DESCRIPTION OF THE PREFERRED EMBODIMENTS

Figure 1:
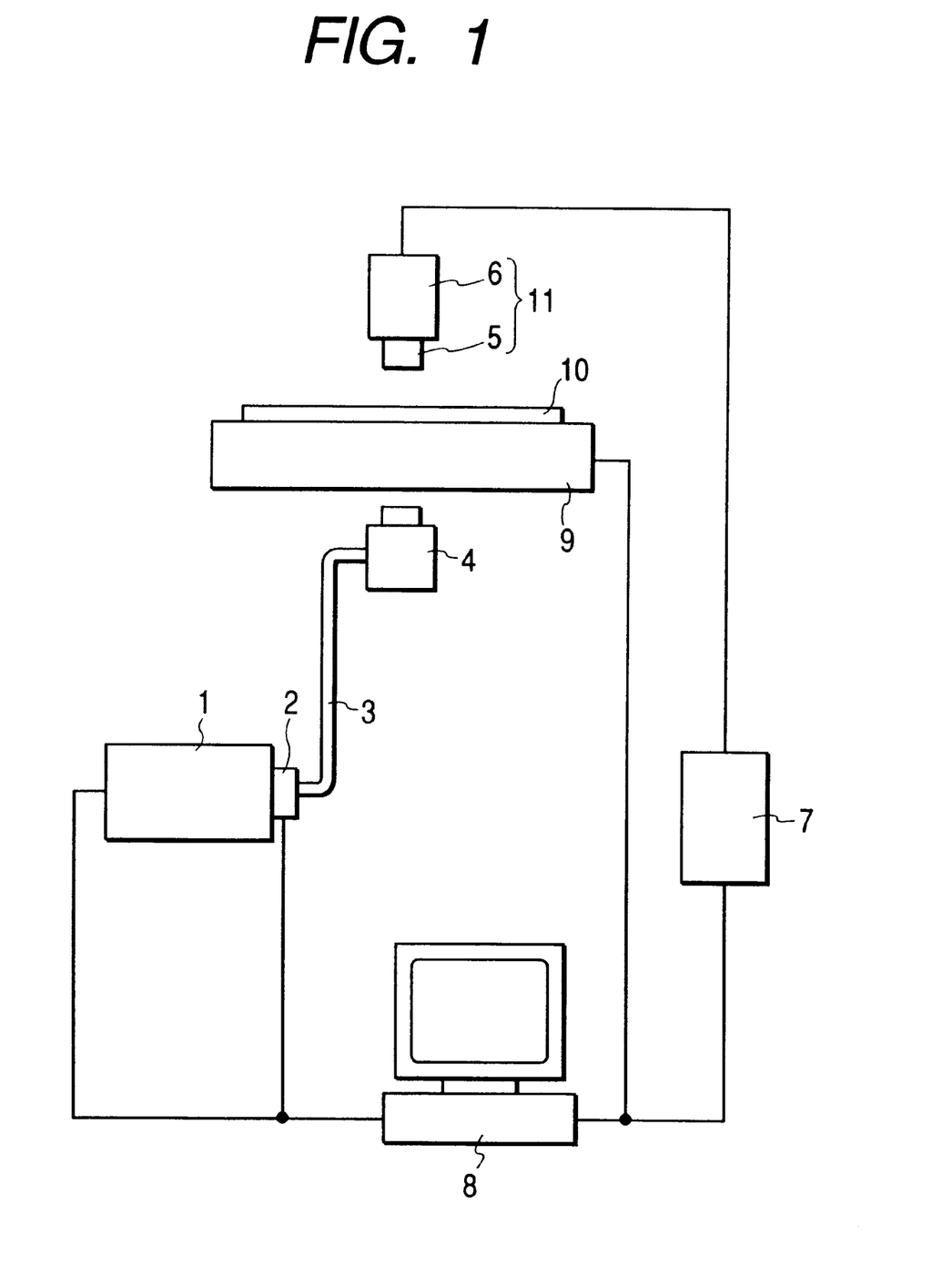
FIG. 1 is a schematic diagram showing the construction of an embodiment of an inspecting device used in the present invention.

FIG. 1 is a schematic diagram showing the construction of an embodiment of an inspecting device of the present invention. In FIG. 1, reference numerals 1, 2 and 3 respectively designate a light source, an optical element for adjusting a light amount, and a light guide. Reference numerals 4, 5 and 6 respectively designate an optical path adjusting system for adjusting the optical path of an incident light with respect to a light receiving element 11, an optical system for enlarging an image, and a CCD camera for inputting the image of a measuring object to an image processing unit 7. In this embodiment, the light receiving element 11 according to the present invention is constructed by the optical system 5 and the CCD camera 6. Reference numeral 9 designates an XY control stage for mounting a color filter thereto. The XY control stage 9 is made to have transparency so that a transmitting light source from below can be utilized. Otherwise, the XY control stage 9 is arranged in an opening portion in a measuring area. Reference numeral 10 designates a color filter as an inspecting object. The image processing unit 7 measures a transmitting light amount for every coloring portion. An operation of the image processing unit 7 is controlled by a personal computer 8 (referred to as PC). The PC 8 can also control the light amount of the light source 1 and an operation of the XY control stage 9 by using an RS232C or GPIB interface.

In the present invention, halogen, etc., metahalide, etc., a mercury lamp, a xenon light source, etc. are preferably used as the light source 1, but the light source 1 is not limited to these members. According to the present invention, "light amount of the light source being set substantially constant" means that the light amount change is within ±5%, and desirably within ±1%.

As the optical element 2 is constructed by using an optical element capable of changing transmittance (e.g., a combination of polarizing elements, a slit, a pin hole, etc.), or an optical element having a constant transmittance (e.g., an ND filter, a mirror, a lens, a mesh diaphragm, etc.). For example, the latter is constructed such that elements for respective coloring portions of R, G and B and a non-display portion (reference) are combined with each other in accordance with the measuring object and are suitably switched and used.

Figure 3:
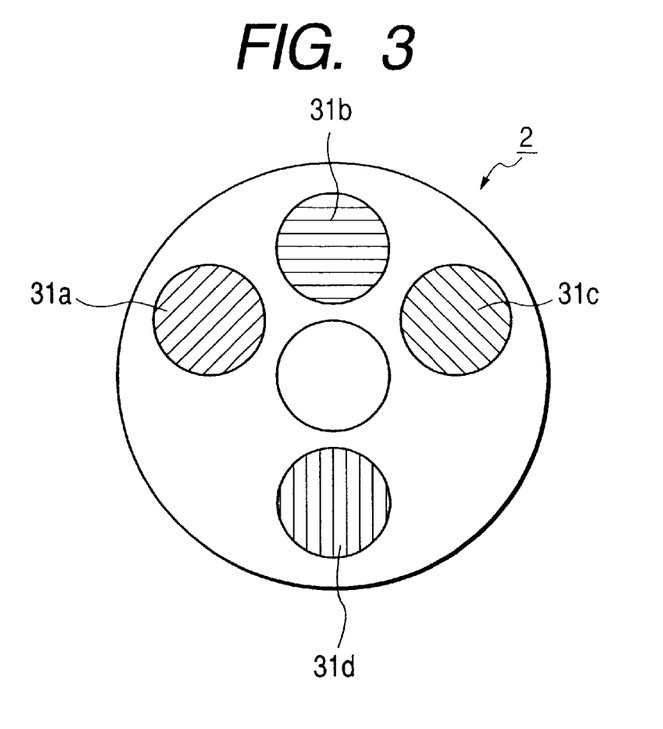
FIG. 3 is a schematic diagram showing the construction of one example of an optical element used in the present invention.

FIG. 3 shows an example of the optical element constructed by using in combination a plurality of elements having a constant transmittance, described above. This optical element is constructed by using four kinds of ND filters. Reference numerals 31a, 31b and 31c respectively designate filters for the coloring portions of R, G and B. Reference numeral 31d designates a filter for reference. Transmittances of the respective filters are determined such that a amount of incident light that enters to the CCD camera at the time of measurement ranges from 50% to 100%, desirably from 60% to 90%, further desirably from 70% to 80% of a light amount providing a full output of the CCD camera. In this case, it is needless to say that an ND filter having the largest transmittance may be replace by, simply, an opening (transmittance 100%). Switching between these filters 31a to 31d is controlled by the PC 8 and is synchronized with measurement of the measuring object.

In this embodiment, the amount of incident light that enters to the color filter 10 is adjusted by the optical element 2. When the transmittance of the optical element 2 is variable, the measurement is made while the transmittance is suitably adjusted. When the optical element 2 is constructed by using in combination elements of constant transmittance, the measurement is made while these elements of the optical element 2 are suitably switched from one to another. The device uses either variable type or constant type. Alternatively, the device may use in combination a plurality of variable transmittance elements and constant transmittance elements. In this embodiment, the optical element 2 is arranged just behind the light source 1 within the optical path. However, position of the optical element 2 is not limited thereto. When a plurality of optical elements are used, these optical elements can be arranged in plural positions.

In the construction of FIG. 1, the light source 1 is arranged in a position apart from the XY control stage 9, so that the light guide 3 is used. Alternatively, the light source 1 may be arranged such that the XY control stage 9 is directly irradiated with the light.

An area sensor type CCD camera is generally suitable for the CCD camera 6 used in the present invention. On the other hand, a line sensor type CCD camera can be also used as the CCD camera 6. In either case, both a color type and a black-and-white type may be used. Further, the present invention is not limited to the use of the CCD camera, but other light receiving element may be also used.

Figure 4:
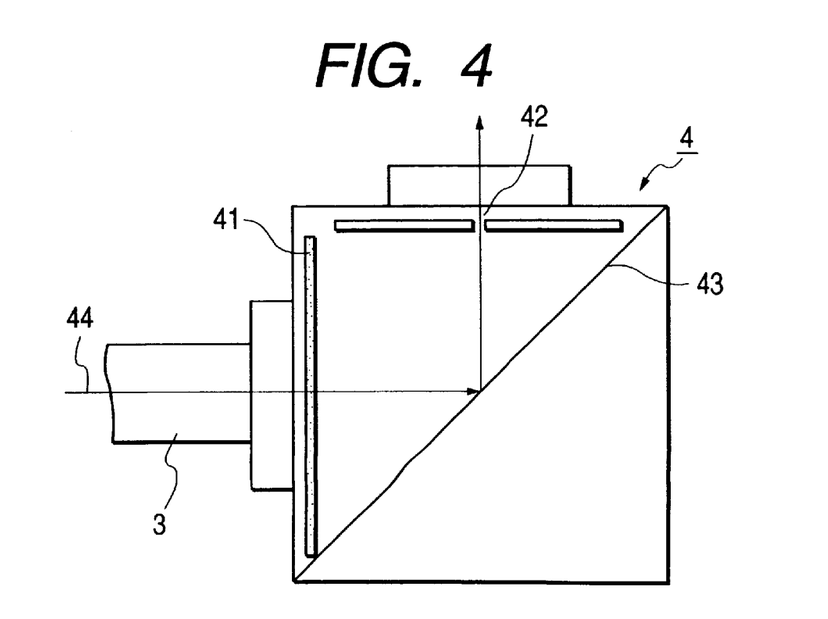
FIG. 4 is a sectional view schematically showing the construction of an example of an optical path adjusting system usable in the present invention.

FIG. 4 shows the construction of an example of the optical path adjusting system 4 of FIG. 1. In FIG. 4, reference numerals 41, 42 and 43 respectively designate a light diffusing element, a pin hole and a reflecting mirror. Light 44 from the light source is diffused by the light diffusing element 41 and the optical path thereof is adjusted by the reflecting mirror 4. A required amount of diffused light is taken out through the pin hole 42 and a light amount distribution on a face is uniformed.

Figure 2:
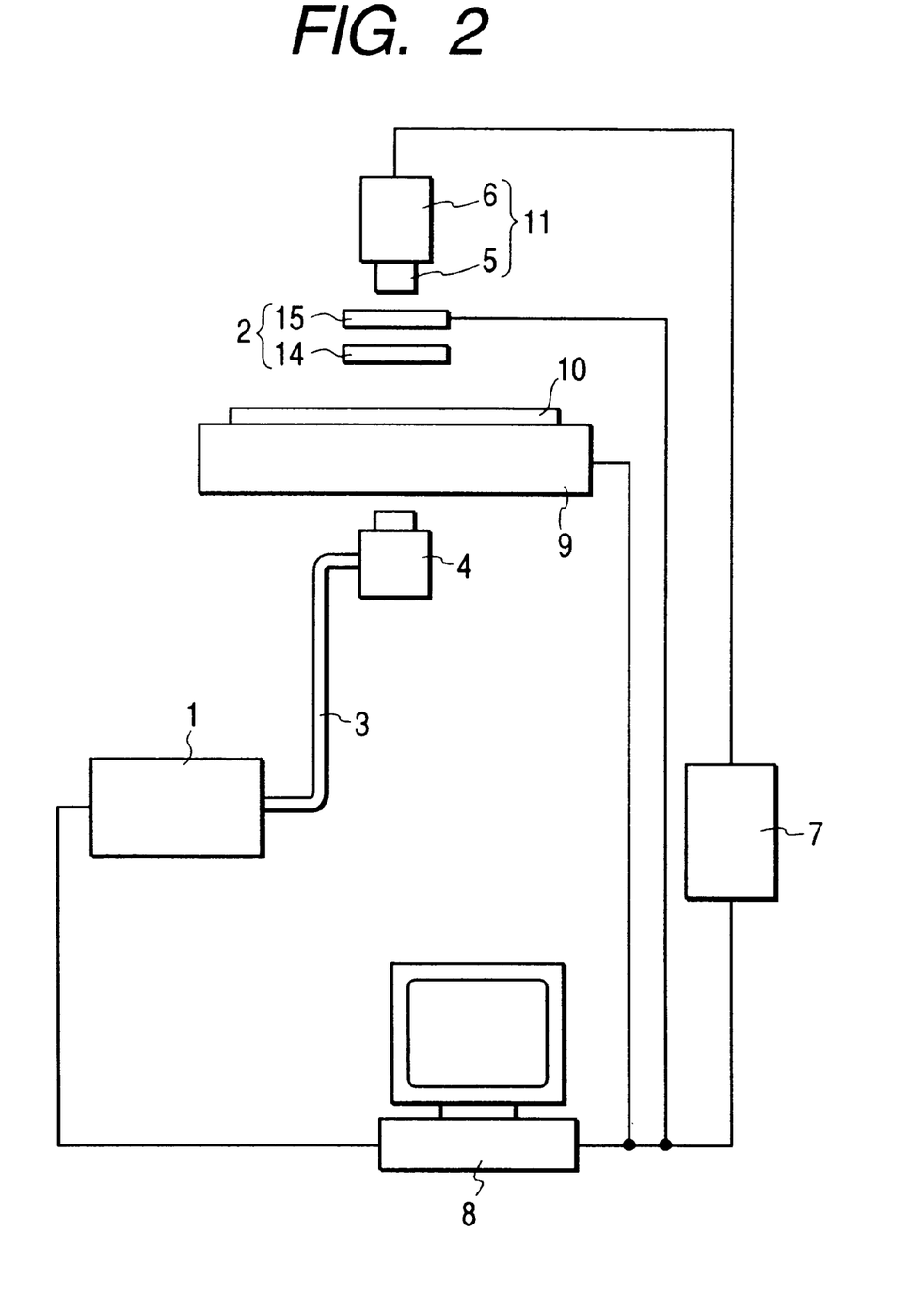
FIG. 2 is a schematic diagram showing the construction of another embodiment of the inspecting device used in the present invention.

FIG. 2 is a schematic diagram showing the construction of another embodiment of the inspecting device of the color filter according to the present invention. In this embodiment, a transmitting light amount transmitted through the color filter is adjusted by the optical element. In this example, a combination of polarizers having variable transmittance is used as the optical element 2. In this figure, reference numerals 14 and 15 designate polarizers. One polarizer 14 is fixed so that light of constant polarization is transmitted through this polarizer 14, and the other polarizer 15 is rotated. Thus, a light amount transmitted through these polarizers can be continuously adjusted. It is desirable to arrange these two polarizers such that these polarizers are not spaced from each other, but are adjacent to each other (since there is a possibility in that, when these polarizers are spaced from each other and another optical element, etc. are arranged between these polarizers, polarizing planes are changed by the influence of this arrangement). The polarizer 15 is attached to a θ-controllable holder and its θ-rotation is controlled by the PC 8.

The above constructions of FIGS. 1 and 2 can be also combined with each other.

A procedure for measuring uneven coloring of the coloring portion of the color filter by using the inspecting device of FIG. 1 will next be explained. In this case, an element constructed by four kinds of ND filters shown in FIG. 2 is used as the optical element 2.

Figure 5:
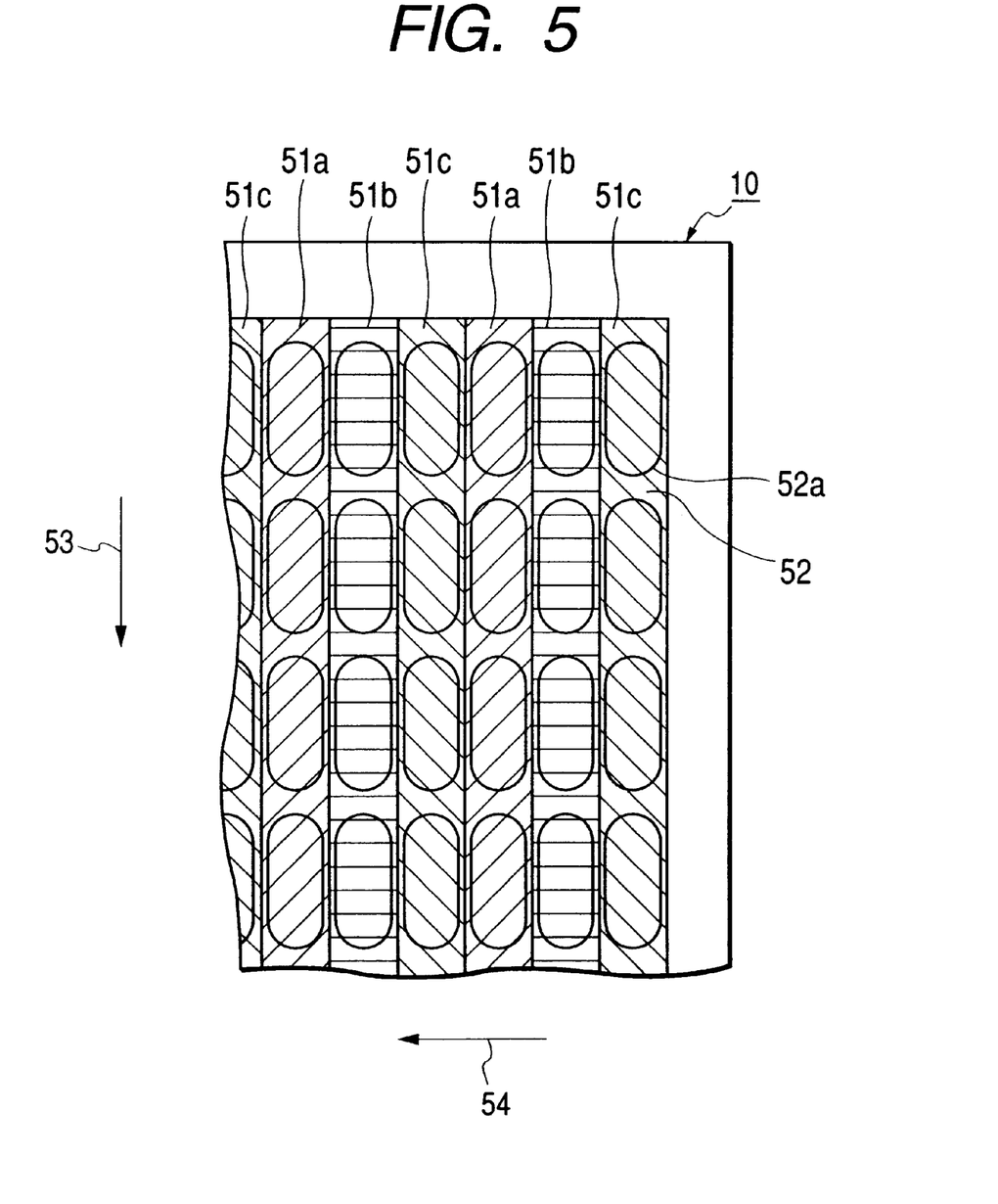
FIG. 5 is a plan view schematically showing an example of a color filter to be inspected in accordance with the present invention.

FIG. 5 is a typical plan view showing the construction of one example of the color filter inspected by the present invention. The color filter is colored by drawing line images in the direction of an arrow 53 by an ink jet system. In this figure, reference characters 51a to 51c respectively denote coloring portions of R, G and B. Reference characters 52 and 52a respectively denote a black matrix and an opening portion formed in the black matrix 52.

(1) The KY control stage 9 is moved to a position in which the CCD camera 6 picks up the image of an uncoloring portion (an area except for the coloring portions 51a to 51c). At this time, an automatic switching type ND filter is simultaneously switched to the filter 31d for reference in advance.

(2) A transmitting light amount is substantially adjusted to a constant value by adjusting the light amount of the light source (reference light amount adjustment). This constant value is set to range from 50% to 100%, preferably from 60% to 90%, further preferably from 70% to 80% of a light amount providing a full output of the CCD camera.

(3) Transmitting light of each of the coloring portions 51a to 51c is measured. At this time, the following two examples are used as a measuring method, but the measuring method is not limited to these two examples.

i) One Scanning Measurement (three-color simultaneous measurement)

The XY control stage 9 is moved to a coloring position of a measuring start. Thereafter, while the XY control stage is step-fed in a measuring direction 54 every one coloring portion, a switching operation to the ND filter according to each color is simultaneously performed (the feed of the XY control stage and the switching operation of the ND filter are controlled by the PC 8 in synchronization with each other). A transmitting light amount of this ND filter is sequentially inputted and transmittances (luminances or absorbances) of all the coloring portions are measured by one scan.

ii) Three-Scanning Measurement (measurement every color)

For example, the measurement is performed in an order of R, G and B.

First, the XY control stage 9 is moved to a measuring start coloring portion of R (at this time, a synchronizing operation with the automatic switching ND filter is performed by the PC 8 and the filter is switched to the filter 31a for R). Thereafter, the stage is step-fed in the measuring direction 54 every three coloring portions, and transmittance (luminance or absorbance) of only the coloring portion 51a of R is measured. After the measurement of the coloring portion of R is terminated, the stage is returned to a measuring start coloring portion of G and the ND filter is switched to the filter 31b for G. Similar to A, only the coloring portion 51b of G is then measured. A similar scanning operation is also repeated with respect to B. Thus, the transmittance of each of the coloring portions of R, G and B is sequentially measured.

The transmittance in each of the coloring portions is obtained as mentioned above and a distribution of this transmittance means the distribution of a coloring density as it is. If the transmittance of a coloring portion having a coloring density already known in advance is measured and a relation of the transmittance and the coloring density is calculated, the coloring density of this coloring portion can be calculated from the transmittance obtained by the measurement.

A manufacturing procedure of the color filter with the above inspecting results as a determining means of an ink amount will next be explained.

(a) Transmittance is measured in the above inspecting procedure with respect to each coloring portion of the color filter colored in a suitable ink amount. This transmittance becomes a target value.

(b) A coloring operation is performed by distributing the given ink amount several times, and a corresponding relation of an ink changing amount and a transmittance changing amount is obtained from this transmittance. A coefficient for converting the transmittance changing amount to the changing amount of the real ink amount is calculated on the basis of this corresponding relation.

The above contents correspond to a pre-preparation.

(c) The transmittance of a color filter newly colored is measured along the above inspecting procedure and uneven coloring are inspected. A shifting amount of these measuring and inspecting results and the target value of the above (a) is calculated.

(d) A new ink amount is calculated with respect to the shifting amount calculated in the above (c) in consideration of the converting coefficient calculated in the above (b).

(e) The results of the above (d) are fed back to a coloring process of the color filter and the ink amount given por one pixel is controlled. When the coloring process of the color filter using an on-demand type ink jet head is used, the ink amount is generally controlled by using an interval of ink droplets given onto the color filter in addition to a method for controlling the volume of an ink droplet discharged from a nozzle.

The transmittance of the coloring portion is measured by the procedure of the above (1) to (3) in each of operations of the above (a) to (c) so that the uneven coloring of the color filter can be detected for a short time with high accuracy. Accordingly, the ink amount is rapidly controlled and the color filter can be manufactured with high efficiency and good yield.

It is generally desirable to measure coloring portions of other colors by the filter of a color having a largest transmittance in the measurement of the coloring portions without switching the filters (31a to 31d in FIG. 3) for the respective coloring portions so as to perform the inspecting operation for a shorter time. In this case, there is a possibility of a slight reduction in measuring accuracy, but the measuring accuracy is practically sufficient in many cases. In this case, a filter for the coloring portion arranged in the optical element (2 in FIG. 3) is set to one or zero filter, i.e., an opening portion. In an embodiment of the present invention, the filter may be commonly used with respect to only a color of one portion of the coloring portion as an application example.

As explained above, no adjusting time of the light amount of the light source is required in accordance with the present invention so that uneven coloring of the color filter can be efficiently inspected with high accuracy and the coloring density of each coloring portion can be also calculated. Therefore, the ink amount can be precisely controlled for a short time in a manufacturing method of the color filter into which the inspecting method of the present invention is assembled. Therefore, it is possible to more cheaply provide a reliable color filter for improving yield without reducing manufacturing efficiency.

A manufacturing method of the color filter using an ink jet will be explained hereinunder.

For example, the color filter can be manufactured by a series of processes shown in FIGS. 6A to 6F.

In the present invention, a substrate is preferably set to have a light transmitting property and a glass substrate is generally used. However, the substrate is not limited to the glass substrate if the substrate has characteristics such as a transparent property, a mechanical strength, etc. required as a color filter for a liquid crystal.

Figure 6A:
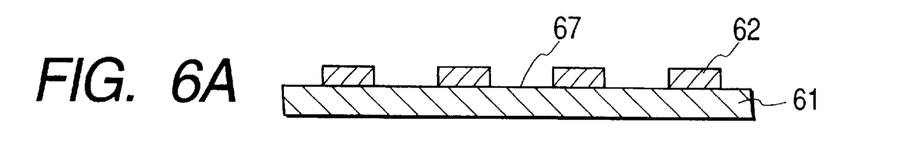
FIGS. 6A, 6B, 6C, 6D, 6E and 6F are process diagrams showing an example of a manufacturing method of a color filter substrate according to the present invention.
Figure 6B:
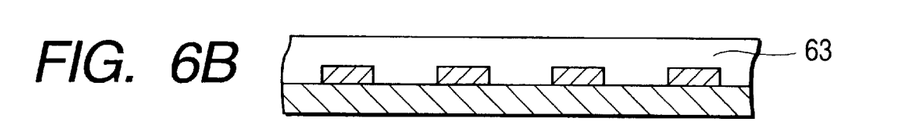

FIG. 6A shows a glass substrate 61 having a light transmitting portion 67 and a black matrix 62 as a light shielding portion. The substrate 61 forming the black matrix 62 thereon is coated with a resin composition. The resin composition can be hardened by light irradiation or the light irradiation and heating so that an ink absorbing property is reduced. In accordance with necessity, a resin layer 63 is formed by prebaking (FIG. 6B). The resin layer 63 can be formed by using a coating method such as spin coat, roll coat, bar coat, spray coat, and dip coat, and the coating method is not particularly limited thereto.

Figure 6C:
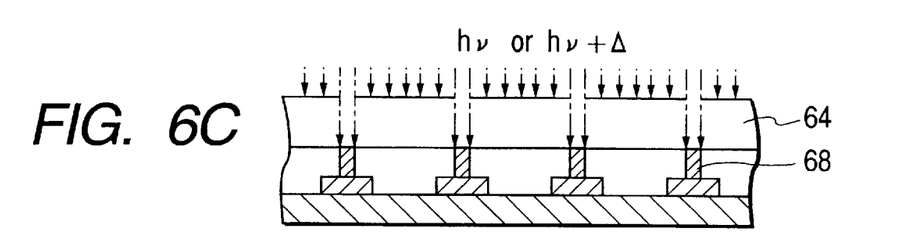
Figure 6D:
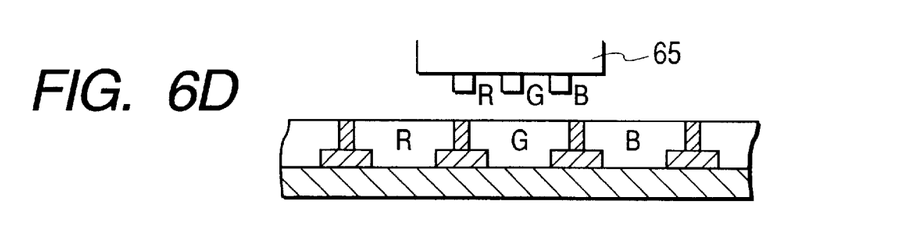

Next, a pattern of the resin layer of a portion light-interrupted by the black matrix 62 is exposed in advance by using a photomask 64 so that one portion of the resin layer is hardened and a portion 68 unabsorbing ink (an uncoloring portion) is formed (FIG. 6C). Thereafter, the same layer is colored in each color of R, G and B by using an ink jet head 65 (FIG. 6D) and the ink is dried in accordance with necessity.

A member having an opening portion for hardening the light-shielding portion formed by the black matrix is used as the photomask 64 used in the pattern exposure. In this case, it is necessary to give a relatively large amount of ink so as to prevent the decoloration of a coloring agent in a portion coming in contact with the black matrix. Therefore, it is preferable to use a mask having an opening portion narrower than a (light shielding) width of the black matrix.

Both a coloring matter system and a pigment system can be used as ink used in coloring. Both liquid ink and solid ink can be also used as the ink used in coloring.

A material having an ink receiving property and able to be hardened by at least one processing of light irradiation or the light irradiation and heating can be used as the resin composition able to be hardened and used in the present invention. For example, this resin is constructed by acrylic resin, epoxy resin, silicon resin, a cellulose derivative such as hydroxypropyl cellulose, hydroxyethyl cellulose, methyl cellulose, carboxymethyl cellulose, etc., or its modified substance, etc.

An optical starting agent (crosslinking agent) can be also used to progress a crosslinking of these resins by light or light and heat. Bichromate, a bisazide compound, a radical system starting agent, a cation system starting agent, an anion system starting agent, etc. can be used as the optical starting agent. The optical starting agent can be also used by mixing these optical starting agents with each other, or combining these optical starting agents with another sensitizer. Heat treatment may be also taken to further progress the crosslinking after the light irradiation.

The resin layer including these compositions is very excellent in heat resistance, water resistance, etc., and can be sufficiently bear high temperature in a subsequent process or a washing process.

A bubble jet type using an electricity-heat converting body as an energy generating element, a piezo jet type using a piezoelectric element, etc. can be used as the ink jet system used in the present invention. A coloring area and a coloring pattern can be arbitrarily set.

Figure 6E:
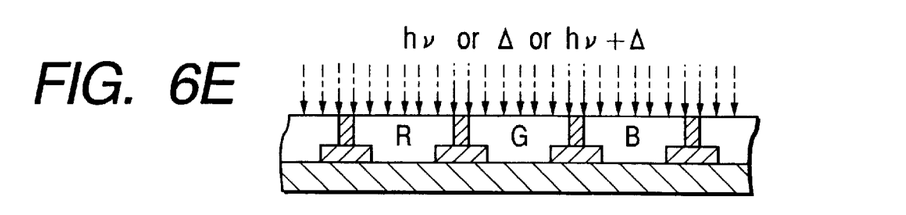

Next, the resin composition is hardened by light irradiation or the light irradiation and thermal irradiation (FIG. 6E). After the resin composition is hardened, the coloring density of a coloring portion is inspected by the inspecting method of the present invention. It is not necessary to inspect the coloring density with respect to all color filters.

Figure 6F:
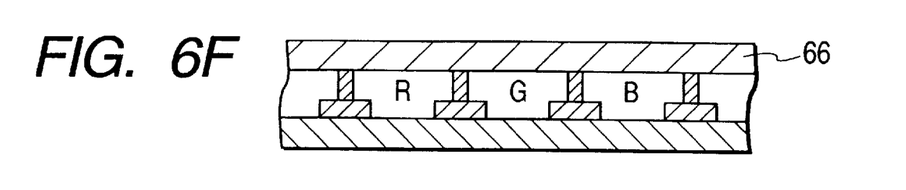

Thereafter, a protecting layer 66 is formed in accordance with necessity (FIG. 6F). The protecting layer 66 can be formed by using a second resin composition of an optical curing type, a heat curing type or a curing type using both light and heat. Otherwise, the protecting layer 66 can be formed by evaporation or sputtering using an inorganic material. If a material has a transparent property when this material is set to a color filter, and this material sufficiently bears subsequent ITO forming process and orientation film forming process, etc., this material can be used as the protecting film.

FIGS. 7A to 7E show another example of the color filter of the present invention.

Figure 7A:
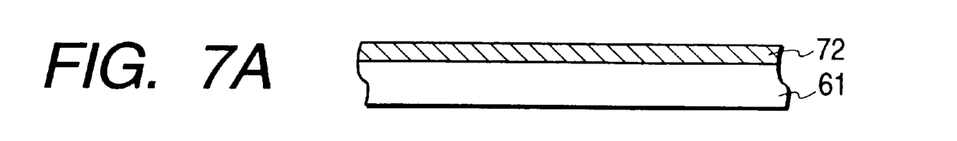
FIGS. 7A, 7B, 7C, 7D and 7E are process diagrams showing another example of the manufacturing method of the color filter substrate according to the present invention.

(a) A transparent substrate 61 is coated with a black photosensitive resin composition 72. The coating film has a thickness capable of obtaining a required light shielding property, e.g., a thickness of about 1 $\mu$m. For example, glass is used in the transparent substrate in many cases, but a plastic film and a plastic sheet may be also used in the transparent substrate. A thin film for improving a close contact property can be also formed on the transparent substrate in advance to improve a close contact property of the transparent substrate, the black matrix and the coloring ink in accordance with necessity.

Figure 7B:
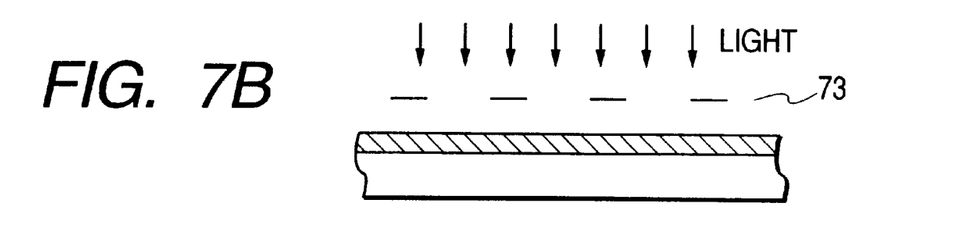

(b) For example, the coated layer is temporarily hardened by a hot plate, etc., and is exposed by using an exposure device having a wavelength in conformity with a sensitivity of the photosensitive resin composition and a mask 73 having a predetermined pattern.

Figure 7C:
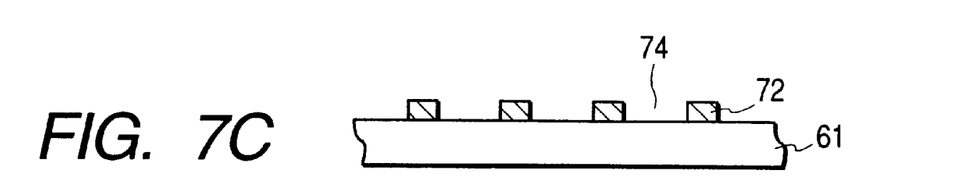

(c) When a developing operation is performed, a portion light-interrupted by the mask 73 is eluted by a developing liquid at an exposure time if it is a negative type. Thus, a substrate surface is exposed and the exposure portion is left as a black matrix pattern. The substrate is subsequently rinsed to wash away the developing liquid and is simply dried by spin drying, an air knife, etc. Thus, the substrate surface of a clearance 74 of the black matrix is set to a clean surface.

Figure 7D:
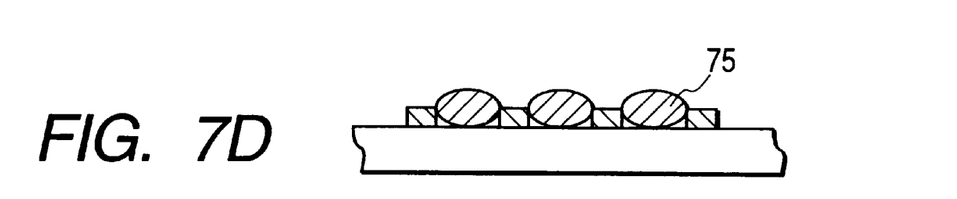

(d) Ink 75 of a predetermined color is then given to the black matrix clearance portion 74. The ink 75 can be given by using a general printing method such as offset printing, gravure printing, screen printing, etc. In particular, in accordance with an ink jet printing method using an ink jet printing machine, no printing block is used at a printing time so that patterning can be preferably performed with high accuracy if the diameter of an ink droplet is adjusted. The ink is used here by suitably selecting a material which tends to be repelled on the above black matrix pattern and tends to be wet in a pixel portion of the black matrix clearance. Surface energy (surface tension) is normally set to range from 30 to 70 dyne/cm. Such ink may be formed by one of a dyeing system and a pigment system and a solvent may also include a hydrophilic organic solvent, etc. with water as a main component.

It is preferable to use heat curing ink as the ink since hardening of the ink and main hardening of the black matrix are performed by the same process.

A heat curing component included in the ink is preferably formed by a material for hardening the ink approximately in the same temperature condition as the main hardening of the black matrix. For example, this material can be constructed by suitably using acrylic system resin, epoxy system resin, phenol system resin, enthiol, etc. Further, this material can be also constructed by using an aromatic amine system, acid anhydride, etc. introduced in the above resins in accordance with a required process temperature.

Figure 7E:
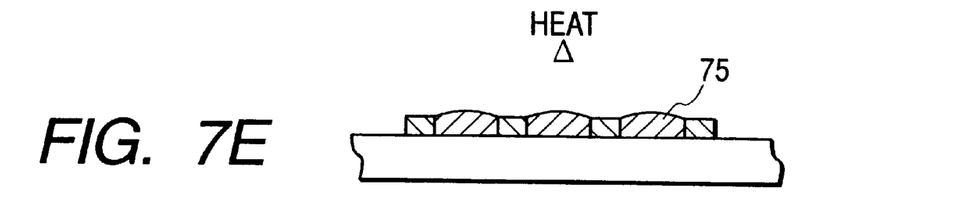

(e) Heat drying processing (post bake) is performed to mainly harden the black matrix and the black matrix is formed. At this time, it is preferable to simultaneously mainly harden the ink.

After the post bake, the coloring density of the coloring portion is inspected by the inspecting method of the present invention. Thereafter, a protecting layer is formed in accordance with necessity.

Figure 8:
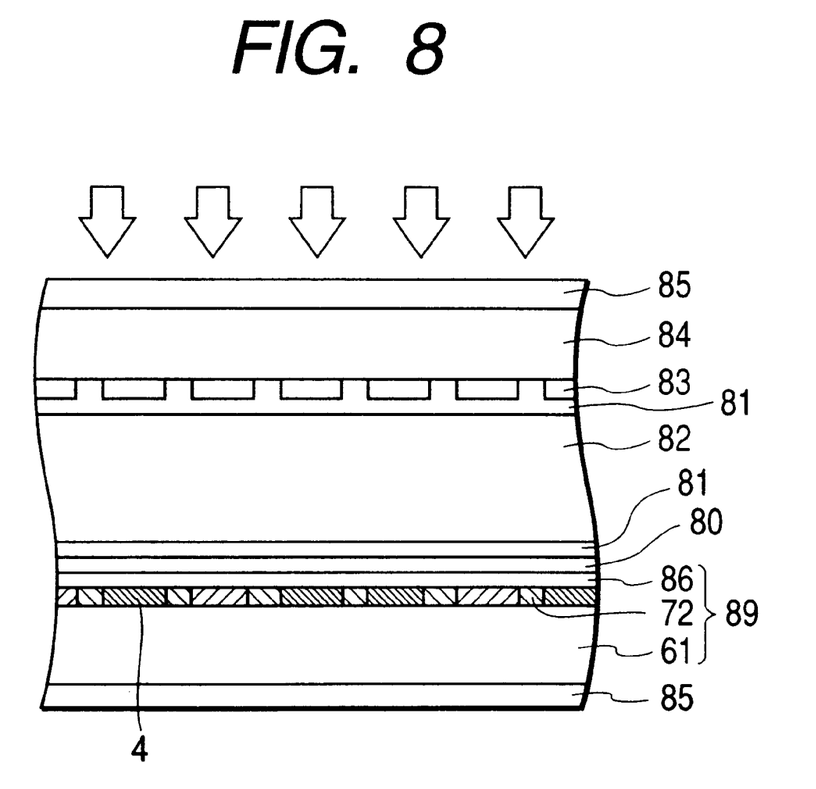
FIG. 8 is a sectional view showing an example of a liquid crystal display unit of the present invention.

FIG. 8 shows the cross section of a TFT color liquid crystal panel into which the color filter is assembled by a coating device of the present invention. The form of this color liquid crystal panel is not limited to this example.

The color liquid crystal panel is generally formed by combining a color filter substrate 61 and an opposite substrate 84 with each other and sealing a liquid crystal composition 82 between the color filter substrate 61 and the opposite substrate 84. An unillustrated TFT and a transparent pixel electrode 83 are formed in a matrix shape inside one substrate 84 of the liquid crystal panel. A color filter 89 is arranged inside another substrate 61 such that coloring materials of RGB are arranged in positions opposed to the pixel electrode. A transparent opposite electrode (a common electrode) 80 is formed on an entire surface of this color filter 89. The black matrix is normally formed on a color filter substrate side. An orientation film 81 is further formed on faces of both the substrates. Liquid crystal molecules can be arranged in a constant direction by performing rubbing-processing of this orientation film 81. A polarizing plate 85 is adhered to an outer side of each of the glass substrates. A clearance (about 2 to 5 µm in size) of these glass substrates is filled with a liquid crystal compound 82. A combination of an unillustrated fluorescent light and an unillustrated scattering plate is generally used as a back light. The liquid crystal compound functions as an optical shutter for changing transmittance of light of the back light so that a display operation is performed. Reference numeral 86 designates a protecting layer.

What is claimed is:

1. An inspecting method of a color filter, comprising:

irradiating with light from a light source a coloring portion;

measuring a transmitting light amount transmitted through the coloring portion by a light receiving element; and calculating a coloring density of the coloring portion, wherein:

the light amount of the light source is set substantially constant;

the amount of incident light received by the light receiving element is adjusted by an optical element arranged within an optical path;

the transmitting light amount of an uncoloring portion is measured; and the coloring density of the coloring portion is inspected by comparing the transmitting light amount of the coloring portion to the transmitting light amount of the uncoloring portion.

2. An inspecting method of a color filter according to claim 1, wherein the light amount is adjusted by the optical element in the measurement of the uncoloring portion, and the light amount adjustment by the optical element is not performed in the measurement of the coloring portion.

3. An inspecting method of a color filter according to claim 1, wherein the light amount is adjusted by using the optical element in each of the measurements of the uncoloring and coloring portions.

4. An inspecting method of a color filter according to claim 3, wherein the light amount is adjusted by using the optical element for every color of the coloring portions.

5. A manufacturing method of a color filter substrate, comprising the steps of;

forming black matrix patterns on a substrate;

applying coloring ink to clearances of the black matrix patterns; and inspecting the coloring density of a coloring portion by an inspecting method according to claim 1, wherein an ink amount per pixel is determined when next applying the coloring ink on the basis of the results of the inspection.

6. A liquid crystal display element comprising a color filter substrate manufactured by the method according to claim 5, an opposite substrate arranged oppositely to the color filter, and a liquid crystal composition sealed between the color filter substrate and the opposite substrate.

\* \* \* \* \*